US00PP23558P2

(12) United States Plant Patent
Kordes

(10) Patent No.: US PP23,558 P2
(45) Date of Patent: Apr. 23, 2013

(54) FLORIBUNDA ROSE PLANT NAMED 'KORFLOCI23'

(50) Latin Name: *Rosa hybrida*
Varietal Denomination: KORfloci23

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 13/136,222

(22) Filed: Jul. 25, 2011

(51) Int. Cl.
*A01H 5/00* (2006.01)

(52) U.S. Cl. ..... Plt./148

(58) Field of Classification Search ..... Plt./148, Plt./149

See application file for complete search history.

*Primary Examiner* — Kent L Bell

(57) ABSTRACT

A new and distinct variety of rose with novel pink flowers, and attractive foliage with very good disease resistance. It exhibits bushy growth with abundant glossy foliage. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORfloci23'.

CROSS REFERENCES AND FEDERAL R&D STATEMENT

There are no cross referenced or related applications. This variety was developed without the aid of any research grant.

The new variety of rose plant of the present invention originated from a controlled crossing in a breeding program of two distinct parents during the summer of 1999. The crossing was between 'un-named seedling', a non patented rose, and an 'un-named seedling', a non patented rose.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORfloci23'.

SUMMARY OF THE INVENTION

The new rose plant may be distinguished from its seed parent an 'un-named seedling', by the following combination of characteristics:

1. The flower color of 'KORfloci23' is pink while the flower color of the seed parent is red.
2. The flower size of 'KORfloci23' is medium while the flower size of the seed parent is small.

The new rose plant may be distinguished from its pollen parent, an 'un-named seedling' by the following combination of characteristics:

1. The petal count of 'KORfloci23' is double while the petal count of the pollen parent is very double.
2. The growth habit of 'KORfloci23' is bushy while the growth habit of the pollen parent is compact.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORfloci23' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORfloci23' was selected in May, 2000 from the seedling beds to be asexually propagated for further evaluation. The first asexual propagation of 'KORfloci23' was done by budding to seedling understocks in July, 2000 at the inventor's nursery in Offenseth-Sparrieshoop, Germany.

This initial and other subsequent propagations conducted in controlled environments demonstrate that 'KORfloci23' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORfloci23'.

DETAILED BOTANICAL DESCRIPTION

The following is a description of 'KORfloci23', as observed growing in June, 2011 in a nursery in Jackson County, Oreg. on plants of 4 years of age. Color references are made using The Royal Horticultural Society (London, England) Colour Chart, 2001 except where common terms of color are used.

For a comparison, several physical characteristics of the rose variety 'KORfloci01', a rose variety from the same inventor described and illustrated in U.S. Plant Pat. No. 21,198 and issued on Aug. 17, 2010 are compared to 'KORfloci23' in Chart 1.

CHART 1

| Characteristic | 'KORfloci23' | 'KOR.floci01' |
|---|---|---|
| Flower bud size upon opening: | 35 mm in length and 40 mm in diameter. | 22-25 mm in length and 15-17 mm in diameter. |
| General tonality on open flower | Red-Purple Group N66B. | Blend of Orange Group 27C and Orange Group 27D. |
| Stamens: | Approximately 80 on average. | Flowers are lacking stamens. |

Parents:

*Seed parent*.—An 'un-named seedling'.

*Pollen parent*.—An 'un-named seedling'.

Classification:

*Botanical classification*.—*Rosa hybrida* 'KORfloci23'.

*Commercial classification*.—Floribunda rose.

FLOWER AND FLOWER BUD

Blooming habit: Continuous.

Flower bud:

*Size*.—Upon opening, 35 mm in length from base of receptacle to end of bud and 40 mm diameter at its widest point.

*Bud form*.—Short. Globular.

*Bud color*.—As sepals first unfold, bud color is Red Group 53B. When ¼ open, the upper surface of petals is Red-Purple Group N66D and the lower surface is Red-Purple Group N66D. Guard Petals are Red Group 53B.

*Sepals*.—Color: Upper surface Green Group 138C. Lower surface Green Group 138B. Size: Average 20 mm (l)×8 mm (w). Shape: Triangular. Sepal apex is generally cirrose. Weak foliaceous appendages on three of the five sepals. Apex: Pointed. Base: Flat at union with peduncle. Surface texture: Upper side: Pubescent. Lower surface: Slight pubescence. Margins: Dense pubescence with stipitate glands.

Receptacle:

*Surface*.—Smooth. No pubescence or stipulate glands.

*Color*.—Yellow Group 143B.

*Shape*.—Funnel-shaped.

*Size*.—10 mm (h)×8 mm (w).

Peduncle:

*Surface*.—With fine hairs and stipitate glands.

*Length*.—20 to 25 mm average length.

*Diameter*.—1.5 to 2.5 mm average diameter.

*Color*.—Yellow Group 143B.

*Strength*.—Weak.

*Borne*.—Multiple flower buds per stem, generally 2 to 6.

Flower bloom:

*Fragrance*.—None.

*Duration*.—Long lasting. On the plant 5-7 days. Senesced petals drop away cleanly.

*Size*.—Medium sized for a floribunda rose. When open, the average flower diameter is 35 to 40 mm and the average flower height is 20 mm.

*Form*.—Shape of flower when viewed from the side: Upon opening, upper part: Flattened convex. Upon opening, lower part: Flat. Open flower, upper part: Flat. Open flower, lower part: Flat.

Color:

*Upon opening, petals*.—Outermost petals: Outer Side: Red Group 53B. Inner Side: Red-Purple Group N57C. Innermost petals: Outer Side: Red-Purple Group N57B. Inner Side: Red-Purple Group N57A.

*Upon opening, basal petal spots*.—Basal petal spot, outermost petals: Outer Side: Yellow Group 8A. Inner Side: Yellow Group 8A. Basal petal spot, innermost petals: Outer Side: Yellow Group 1A. Inner Side: Yellow Group 2A.

*After opening, petals*.—Outermost petals: Outer Side: Red-Purple Group N66C, transitions to Red-Purple Group N66A at edges. Inner Side: Red-Purple Group N66C, transitions to Red-Purple Group N66A at edges. Innermost petals: Outer Side: Red-Purple Group N66D, transitions to Red-Purple Group N66B at edges. Inner Side: Red-Purple Group N66D, transitions to Red-Purple Group N66B at edges.

*After opening, basal petal spots*.—Basal petal spot, outermost petals: Outer Side: Yellow Group 1D. Inner Side: Yellow Group 1D. Basal petal spot, innermost petals: Outer Side: Yellow Group 1D. Inner Side: Yellow Group 1D.

General tonality: On open flower Red-Purple Group N66B. No change in the general tonality at the end of the 4$^{th}$ day. Afterwards, general tonality is Red-Purple Group 57B.

Petals:

*Petal count*.—Double. Average Range: Approximately 25-35 petals under normal conditions.

*Petal reflex*.—Petals reflex very slightly.

*Petal edge*.—Entire.

*Petal shape*.—Obovate. Apex shape is obtuse. Shape of base is acute.

*Petal size*.—35-40 mm long; 30-35 mm wide.

*Thickness*.—Average.

*Petal arrangement*.—Not formal.

Petaloids: Limited numbers of petaloids.

*Petaloid count*.—Average of 3-6 per flower.

*Petaloid margin*.—Variable, entire to erose.

*Petaloid texture*.—Glaucous.

*Petaloid shape*.—Entire petaloid: Irregularly shaped obovate to subulate. Apex: Obtuse. Base: Obtuse.

*Petaloid size*.—Petaloids are 10 mm (l)×5 mm (w).

*Petaloid color*.—Color of inner side is Red Purple Group 65A. Color of outer side is Red-Purple Group N66C.

Reproductive organs:

*Pistils*.—Average. Approximately 45 present. Stigmas: Location: Slightly superior in position to anthers. Color: Green-Yellow Group 162B. Styles: Length: About 8 mm long. Color: Yellow-White Group 158C.

*Stamens*.—Approximately 80 on average and regularly arranged. Anthers: Size: About 1.5 mm long. Pollen: Generally present. Color: Greyed-Orange Group 167A. Filaments: Color: Yellow Group 8B. Length: About 6 mm.

*Hips*.—Forming seed hips. Color: Yellow Group 146B, transitions to Orange-Red Group N34A with hues of Orange Group N25A. Hip Size: 12-15 mm (h)×12-15 mm (w).

THE PLANT

Growth: Moderately vigorous.

Plant habit: Bushy habit. When grown as a budded field grown plant, the average plant height is 50-65 cm and the average plant width is 30-50 cm.

Stems:

*Stem color*.—Anthocyanin: Greyed-Red Group 181B. Young wood: Yellow-Green Group 144A. Older wood: Yellow-Green Group 144A.

*Stem surface*.—Young wood: Smooth. Older wood: Smooth.

Prickles: Present.

*Incidence*.—8-12 per each 10 cm of stem.

*Size*.—Average length: 5-7 mm.

*Color*.—Immature prickles: Greyed-Purple Group 185A. Mature prickles: Greyed-Purple Group 182A. Senescing to Greyed-Orange Group 174A.

*Shape*.—Concave.

*Anthocyanin*.—Abundant in juvenile thorns, diminishing as thorns mature. Color is Greyed-Purple Group 185A in juvenile thorns and Greyed-Purple Group 182A in mature thorns.

Leaves and leaflets: Normally 7 leaflets on normal leaves in middle of the stem.

*Venation pattern*.—Pyramidal net pattern.

*Leaf size*.—110 mm (l)×75 mm (w).

*Abundance*.—Average.

*Texture*.—Thick and moderately rugose. Upper side of leaflet: Glossy and smooth. Under side of leaflet: Matte.

*Color, mature foliage*.—Upper Leaf Surface: Yellow-Green Group 147A. Lower Leaf Surface: Green Group 137C.

*Color, juvenile foliage*.—Upper Leaf Surface: Green Group 141A. Lower Leaf Surface: Green Group 143B. Anthocyanin: Present. Intonations present on upper leaf margins, veins, and lower side. Color is Greyed-Purple Group 183A.

Stipules:

*Size*.—On average 22-25 mm long. 7-9 mm between the tips of the stipules. Main body of stipule 4-5 mm in width.

*Stipule color*.—Yellow-Green Group 147B.

*Anthocyanin*.—Greyed-Red Group 181B.

*Stipitate glands*.—Present.

*Margins*.—Smooth.

*Shape*.—Apex: Apiculate. Base: Flat.

Petiole:

*Length*.—25-30 mm, on average.

*Diameter*.—1.5-2.5 mm, on average.

*Petiole color*.—Yellow-Green Group 144A.

*Underneath*.—Smooth. Yellow-Green Group 144A.

*Margins*.—With many stipitate glands.

*Anthocyanin*.—Greyed-Red Group 183B.

*Prickles*.—None observed.

Petiole rachis:

*Length*.—40-45 mm, on average.

*Diameter*.—About 2 mm.

*Color*.—Yellow-Green Group 144A.

*Anthocyanin*.—Greyed-Red Group 181B on immature foliage.

*Margins*.—With limited numbers of stipitate glands.

*Prickles*.—None observed on juvenile foliage, some mature foliage exhibits 2-3 per rachis.

*Stipitate glands*.—Very few observed.

Leaflets:

*Size*.—Average size of the terminal leaflet is 35 mm (l)×25 mm (w).

*Shape*.—Entire leaflet: Ovate. Base: Ovate. Apex: Acute.

*Margins*.—Finely serrated.

*Texture*.—Leathery.

Winter hardiness: To date, the variety has been grown successfully in Zone 5.

Disease resistance: Very good resistance to Powdery mildew (*Sphaerotheca pannosa*), rust (*Phragmidium disciflorum*), and blackspot (*Diplocarpon rosae*) diseases under normal growing conditions.

I claim:

1. A new and distinct variety of rose plant, as described and illustrated herein.

* * * * *

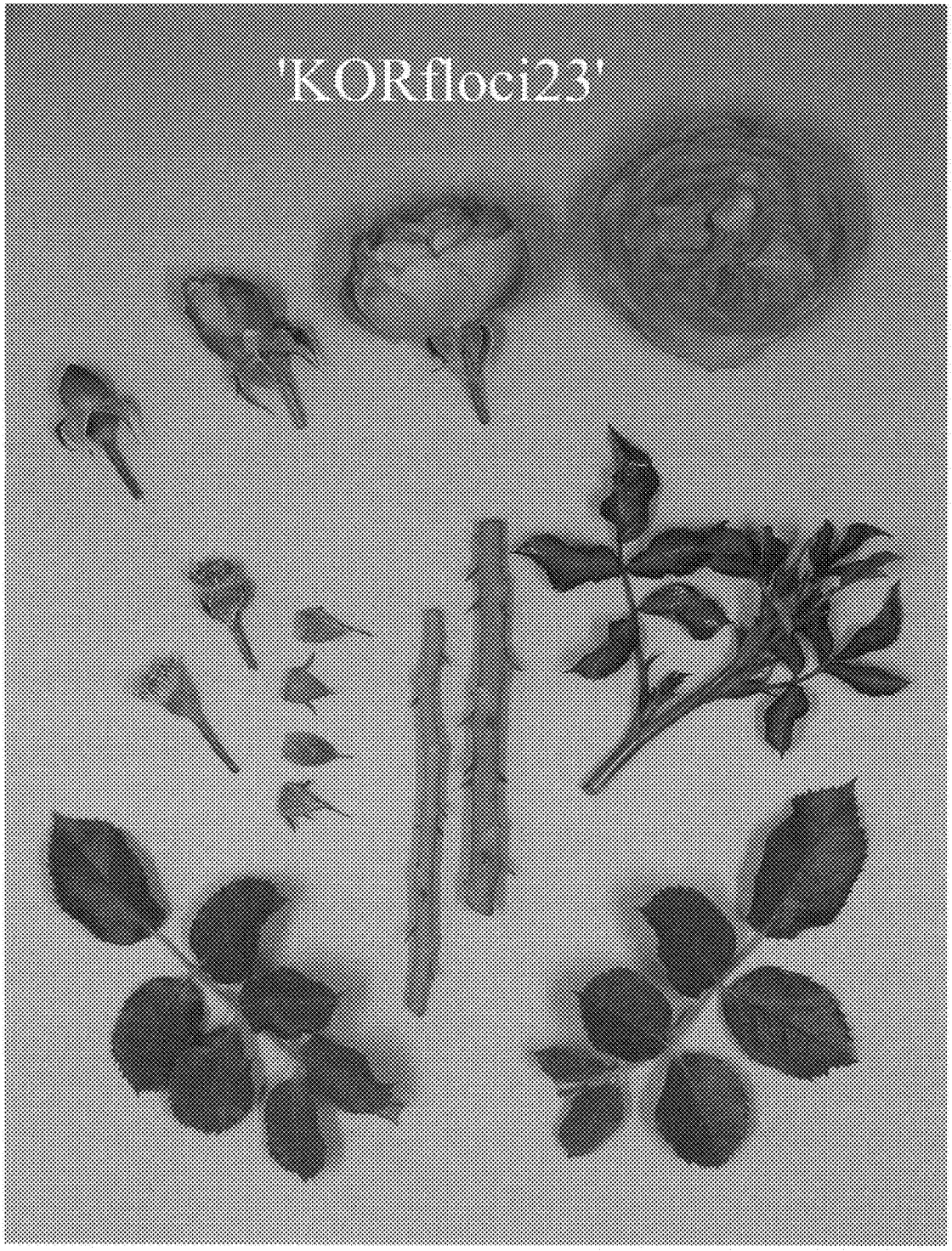
'KORfloci23'